(12) United States Patent
Kuwabara (10) Patent No.: US 6,396,899 B2
(45) Date of Patent: May 28, 2002

(54) FLUORESCENT X-RAY ANALYZING APPARATUS AND SECONDARY TARGET DEVICE DISPOSED THEREIN

(75) Inventor: Shoji Kuwabara, Ibaraki (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/826,846

(22) Filed: Apr. 6, 2001

(30) Foreign Application Priority Data

Apr. 21, 2000 (JP) ........................................ 2000-120307

(51) Int. Cl.⁷ ............................................ G01N 23/223
(52) U.S. Cl. ............................................. 378/45; 378/143
(58) Field of Search ............................... 378/44–50, 143

(56) References Cited

U.S. PATENT DOCUMENTS 4,260,885 A * 4/1981 Albert ......................... 378/45
6,041,095 A * 3/2000 Yokhin ........................ 378/45

* cited by examiner

*Primary Examiner*—Craig E. Church
(74) *Attorney, Agent, or Firm*—Kanesaka & Takeuchi

(57) ABSTRACT

A fluorescent X-ray analyzing apparatus includes a secondary target device therein. The secondary target device includes a target main body, and an X-ray blocking member for preventing an irradiation of primary X-rays from a X-ray source to a sample. The target main body is formed of plural target members in which secondary target materials are formed on at least target surfaces facing a central axis, and the target members are arranged concentrically to have different distances from the central axis. Accordingly, the primary X-rays do not pass through a space between the target members, and are irradiated only at the target surfaces of the target members. The secondary X-rays from the target surfaces pass through the space between the target members, and reach the sample.

12 Claims, 7 Drawing Sheets

FLUORESCENT X-RAY ANALYZING APPARATUS AND SECONDARY TARGET DEVICE DISPOSED THEREIN

BACKGROUND OF THE INVENTION AND RELATED ART STATEMENT

The present invention relates to a secondary target device which generates secondary X-rays called fluorescent X-rays by irradiating X-rays (primary X-rays) generated from an X-ray source, and a fluorescent X-ray analyzing apparatus in which the fluorescent X-rays generated from the secondary target device are irradiated to a sample, and fluorescent X-rays generated from the sample are used to carry out a qualitative and quantitative analysis.

In a fluorescent X-ray analysis, a wavelength and an intensity of characteristic X-rays generated from a sample by a irradiating X-rays to the sample are measured, to thereby carry out a qualitative and quantitative analysis of elements in the sample. In the fluorescent X-ray analysis, there have been known a direct irradiation method in which X-rays (primary X-rays) generated from an X-ray source are directly irradiated to a sample, and a secondary target method which uses a secondary target.

In the direct irradiation method, primary X-rays generated from an X-ray tube are directly irradiated to the sample, and fluorescent X-rays generated from the sample are detected by an X-ray detector, such as a semiconductor detector. In the direct irradiation method, since it is possible to analyze a wide range of elements, the direct irradiation method is suitable for a detection of unknown micro-elements.

On the other hand, the secondary target method improves a limit of detecting micro-elements by making excited X-rays monochromatic, and in the secondary target method, primary X-rays are irradiated to the secondary target formed of a material which differs from an anode target of an X-ray tube, to thereby generate fluorescent X-rays including characteristic X-rays which are inherent to the secondary target, so that continuous X-rays included in the primary X-rays are decreased. Therefore, a signal-to-noise (S/N) ratio of the fluorescent X-rays from the sample is improved, to thereby improve the limit of detecting the micro-elements.

In the fluorescent X-ray analyzing apparatus, it has been desired to have a wide applicability for both detection of an unknown micro-element and highly sensitive analysis of a specific micro-element, and there has been proposed an analyzing apparatus which can perform both analyses by the direct irradiation method and by the secondary target method by switching these methods.

Conventionally, as a structure for switching the analysis by the direct irradiation method and the analysis by the secondary target method, there has been used a secondary target device and a fluorescent X-ray analyzing apparatus, wherein a secondary target is disposed at a position diverting from a straight line connecting between an X-ray source and a sample in the secondary target device so as not to directly irradiate primary X-rays from an X-ray tube to the sample, so that only secondary X-rays from the secondary target are irradiated to the sample, and in case the primary X-rays are directly irradiated to the sample, an orientation of the X-ray source is changed.

In the secondary target device and the fluorescent X-ray device described above, although the direct irradiation method and the secondary target method are achieved by one apparatus, there have been the following problems. Namely, since a moving mechanism for rotating the X-ray source is necessary, the apparatus becomes a large size. Also, since an X-ray irradiating condition (irradiation angle and irradiation position) by the direct irradiation method does not always coincide with an X-ray irradiating condition by the secondary target method, there is a problem in an accuracy of a correspondence between the measured data by both methods.

Also, there has been proposed a secondary target device and a fluorescent X-ray device as disclosed in Japanese Patent Publication (KOKAI) No. 10-325814, in which a secondary target is disposed on a straight line connecting between an X-ray source and a sample. In a case of using the secondary target and a case of directly irradiating primary X-rays, irradiated X-rays are switched while an orientation of the X-ray source is fixed.

In the conventional secondary target device and the fluorescent X-ray analyzing apparatus, as described above, there are problems, such as an increase of the size of the apparatus, and an accuracy problem in the correspondence between the measured data due to the difference between the X-ray irradiating conditions with respect to the sample.

Also, in the proposed apparatus described above, since the irradiated X-rays can be switched while the orientation of the X-ray source is fixed, a hollow section of the secondary target is formed into a tapered form in which an opening section at an X-ray source side is large and an opening section at a sample side is narrowed. Therefore, primary X-rays from the X-ray source can be irradiated with a large effective solid angle to the secondary target, but an effective solid angle of the secondary target observed from the sample is reduced, and an angle of observing the sample from the secondary target is shallow, so that enough secondary X-rays can not be irradiated to the sample, resulting in difficulty in obtaining a high measurement sensitivity.

Also, in both conventional apparatus and proposed apparatus, since the secondary X-rays expand on a surface of the sample in a relatively large range, it is difficult to limit an irradiation area on the surface of the sample by the secondary X-rays into a very small area, so that these apparatuses can not be applied to an analysis of a minute portion.

Accordingly, the present invention has been made to solve the aforementioned problems, and an object of the invention is to provide a secondary target device in which X-ray irradiating conditions in switching the irradiated X-rays are held constant, to thereby irradiate enough secondary X-rays with respect to a sample and to irradiate the secondary X-rays to a minute portion of the sample.

Another object of the invention is to provide a fluorescent X-ray analyzing apparatus, in which X-ray irradiating conditions in switching the irradiated X-rays are held constant and enough secondary X-rays are retained to thereby improve a detection sensitivity, and to improve a sensitivity of analyzing the minute portion of the sample.

Further objects and advantages of the invention will be apparent from the following description of the invention.

SUMMARY OF THE INVENTION

To achieve the aforementioned objects, in the present invention, an X-ray irradiating condition in case of switching irradiated X-rays is maintained to be constant by disposing an X-ray source, a target main body, and a sample on a straight line, and further, in the structure described above, an effective solid angle of observing a target surface from the X-ray source and an effective solid angle of observing the target surface from a sample irradiation position are substantially enlarged, so that enough secondary X-rays are irradiated to the sample. Accordingly, a high detection sensitivity can be obtained in a fluorescent X-ray analyzing apparatus.

Also, in substantially enlarging the effective solid angles, the secondary X-rays irradiated from a plurality of target surfaces are condensed to an irradiation area of the sample, and an irradiation of the secondary X-rays to an area other than the irradiation area is limited, so that the secondary X-rays are irradiated to a minute portion of the sample. Accordingly, a sensitivity of analyzing the minute portion is increased in the fluorescent X-ray analyzing apparatus. Incidentally, the effective solid angle is a solid angle of observing a predetermined region or surface from a certain point, and in the secondary target device and the fluorescent X-ray analyzing apparatus of the invention, the effective solid angle is formed by treating the target surface as the predetermined region surface.

Therefore, in the target device of the invention, the X-ray source, a sample irradiation position, the target main body having a plurality of target members, and an X-ray blocking member for blocking an irradiation of primary X-rays to the sample irradiation position are arranged on a straight line.

In the target main body, the straight line connecting the X-ray source and the sample irradiation position constitutes a central axis, and the plurality of target members is arranged at positions having different distances from the central axis. In each of the target members, a secondary target material is provided on at least a surface of the target member opposed to the central axis, and the surface described above constitutes a target surface. Incidentally, the secondary target material can be provided on a rear surface of the target member which is not opposed to the central axis, or the entire target member can be formed of the secondary target material, or the target member can be a structure in which the secondary target material is provided on a front surface of an X-ray shielding material as a base or substrate.

The target members can be structured in cylindrical forms, in which a plurality of the target members is disposed on respective circumferences of concentric circles having the straight line connecting the X-ray source and the sample irradiation position as the central axis. Also, as long as the target members have different distances from the central axis, the target members are not limited to the cylindrical shapes, and may be polygonal shapes, or the target members may have a structure in which the target members are disposed only in predetermined diametral directions from the central axis. Also, the target members may be disposed continuously, or separated or dispersed.

In setting the straight line connecting the X-ray source and the sample irradiation position as the central axis, a plurality of the target members is disposed around the diametral direction of the central axis. In case of switching the irradiated X-rays, an X-ray irradiating condition by a direct irradiation method and an X-ray irradiating condition by a secondary target method can be made the same. Incidentally, a disposition of plural target members on the respective circumferences of the concentric circles is an example of the disposition of plural target members around the diametral direction of the central axis.

In this structure, there is formed an effective solid angle of observing the target surface of the target member from the X-ray source or the sample irradiation position. Incidentally, in case the target members are respectively disposed in a direction of a normal line from the central axis to be space away from each other with a predetermined interval therebetween, the effective solid angle constitutes an angle of observing a surface, which is formed in a range of a predetermined distance from a center and extends in a form of a concentric circle, from a certain point. However, in the present invention, the shape is not limited to the concentric circle, and may be selected according to the shapes of the target members and the target surfaces, or the disposition location thereof.

In the secondary target device of the invention, in order to effectively irradiate the secondary X-rays to the sample while the irradiation of the primary X-rays to the sample is being prevented, the primary X-rays from the X-ray source are required not to pass through a space, between the target members and irradiated only to the target surfaces of the target members. Also, the secondary X-rays from the target surfaces are required to pass through the space between the target members and reach the sample irradiation position.

In order to fulfill the above requirements, in the structures of the target main body of the invention, a length of each target member in the central axis direction and a disposition interval in the diametral direction between the adjacent target members are required to satisfy the first condition regarding the primary X-rays and the second condition regarding the secondary X-rays. Here, the first condition constitutes a condition in which an effective solid angle of observing the target surface from the primary X-ray source coincides with an effective solid angle of observing the space between the adjacent target members in the target surface side, and the second condition constitutes a condition in which an effective solid angle of observing the target surface from the sample irradiation position coincides with an effective solid angle of observing the space between the adjacent target members from the sample irradiation position in the target surface side.

Since the target members have the structures as described above, the primary X-rays can be irradiated to the target surfaces without being blocked by the adjacent target members, and the secondary X-rays generated at the target surfaces can reach the sample irradiation position without being blocked by the adjacent target members, to thereby form the effective solid angles of the respective target members. Also, by arranging a plurality of the target members as described above, the respective effective solid angles can be consolidated to have a large effective solid angle which is enlarged as a whole.

Also, in the present invention, the X-ray blocking member is disposed on the central axis. The X-ray blocking member is provided for preventing the primary X-rays generated from the X-ray source from being irradiated to the sample irradiation position, and the X-ray blocking member assures the irradiation of the secondary X-rays to the sample irradiation position.

Further, the fluorescent X-ray analyzing apparatus of the invention constitutes a fluorescent X-ray analyzing apparatus with the target device of the invention, and the fluorescent X-ray analyzing apparatus of the invention is formed of an X-ray source for generating X-rays, a secondary target device of the invention, and an X-ray detector for detecting fluorescent X-rays generated from a sample.

In the fluorescent X-ray analyzing apparatus of the invention, by using the target device of the invention, the X-ray irradiating condition in case of switching the irradiated X-rays can be maintained to be constant, and at the same time, a detecting sensitivity can be improved by obtaining enough secondary X-rays irradiated to the sample.

Also, according to the target device of the invention, by condensing the secondary X-rays with respect to the sample position, the sensitivity of analyzing the minute portion can be increased.

In analyzing the minute portion, it is structured that a shielding member having an opening section, which limits an area of irradiating the secondary X-rays in the sample, on the central axis is provided between the secondary target device and the sample irradiation position. Thus, an irradiation of the secondary X-rays to areas other than the area, to which the secondary X-rays are irradiated, is limited to condense the secondary X-rays to the sample position, to thereby increase the sensitivity of analyzing the minute portion.

Also, one or both of a collimator for directly irradiating the primary X-rays to the sample and a filter for absorbing a part of the primary X-rays are provided, and there is to disposed a driving device for disposing one of the secondary target device, the collimator and the filter on the central axis. The collimator, the filter, or the secondary device is switchably disposed on the straight line connecting between the X-ray source and the sample by the driving device. Accordingly, in case the collimator is disposed, the primary X-rays can be directly at irradiated to the sample, and in case the filter is disposed, X-rays with specific wavelengths in the primary X-rays can be irradiated. Also, in case the secondary target device is disposed, by generating fluorescent X-rays including characteristic X-rays inherent to the secondary targets, continuous X-rays contained in the primary X-rays can be decreased, and a signal-to-noise (S/N) ratio of the fluorescent X-rays from the sample can be improved, to thereby carry out the highly sensitive detection of the micro-elements.

DETAILED DESCRIPTION OF PREFERRED EMBODIMENTS

Hereunder, embodiments of the present invention will be explained with reference to the attached drawings.

Figure 1:
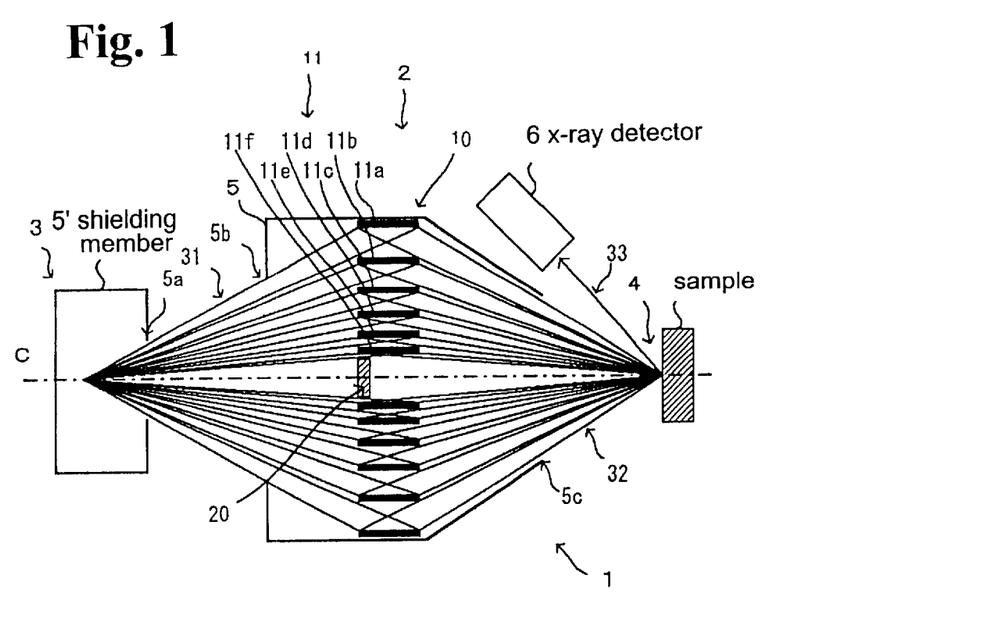
FIG. 1 is a view for schematically explaining a target device and a fluorescent X-ray analyzing apparatus of the invention.

FIG. 1 is a view for schematically explaining a target device and a fluorescent X-ray analyzing apparatus of the invention.

A secondary target device 2 includes a target main body 10 and an X-ray blocking member 20, and is disposed on a central axis C (shown by a single-dotted line in the FIG. 1) connecting between an X-ray source 3 and a sample irradiation position 4. The secondary target device 2 generates secondary X-rays 32 by receiving primary X-rays 31 from the X-ray source 3, and irradiates the secondary X-rays 32 to a sample S disposed at the sample irradiation position 4. Also, a fluorescent X-ray analyzing apparatus 1 includes the target device 2 and an X-ray detector 6 for detecting a characteristic X-ray 33 generated from the sample S by irradiation of the secondary X-rays 32, to thereby measure a wavelength and a strength or intensity of the characteristic X-ray 33, so that the apparatus 1 carries out a qualitative and quantitative analysis of elements in the sample S.

The target main body 10 includes a plurality of target members 11 including 11a, 11b, 11c, 11d, 11e and 11f, and the target members 11a through 11f are disposed radially by respectively changing distances from the central axis C. In the target members 11a through 11f, at least target surfaces thereof facing the central axis C are provided with secondary target materials. On the central axis C, there is disposed the X-ray blocking member 20, which prevents the primary X-rays 31 generated in the X-ray source 3 from reaching the sample irradiation position 4, and only the secondary X-rays 32 generated at the target surfaces are irradiated to the sample S.

Incidentally, the X-ray source 3 is formed of, for example, a heater radiating thermoelectrons and an anode target which generates the primary X-rays 31 by collisions with the thermoelectrons, and the anode target may be formed of a material, such as rhodium (Rh), chromium (Cr), copper (Cu), molybdenum (Mo), and tungsten (W). Also, the target members 11 may be made of a material corresponding to the desired characteristic X-ray, such as aluminum (Al), copper (Cu), germanium (Ge), yttrium (Y) and tin (Sn).

Further, in the X-ray source 3 and the target main body 10, there are disposed shielding members 5', 5 for shielding the primary X-rays 31 and the secondary X-rays 32. The shielding member 5'provided in the X-ray source 3 has an opening section 5a through which the central axis C passes in order to radiate the primary X-rays 31 generated in the X-ray source 3 toward a sample side. Also, the shielding member 5 provided in the target main body 10 has an opening section 5b through which the central axis C passes to irradiate the primary X-rays 31 only to the target members 11 such that the primary X-rays 31 are not irradiated to the sample S, and an opening section 5c through which the central axis C passes, to condense the secondary X-rays 32 generated in the target members 11 to the sample irradiation position 4. At the same time, the shielding member 5 provided in the target main body 10 shields the secondary X-rays 32 such that the secondary X-rays 32 do not reach the X-ray detector 6.

Incidentally, the X-ray blocking member 20 and the shielding members 5, 5' can be formed of an X-ray shielding material, such as lead (Pb).

Figure 2:
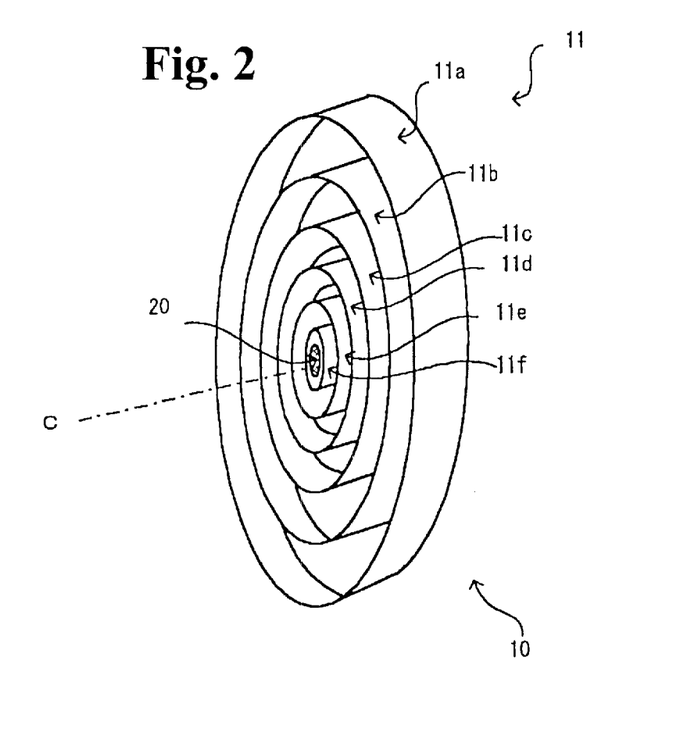
FIG. 2 is a schematic view for showing an example of a target main body of the invention.

FIG. 2 is a schematic view for showing a first example of the target main body. The target main body 10 in the first example includes the target members 11a through 11f, which have cylindrical shapes with different diameters and are disposed in the forms of concentric circles around the central axis C. The X-ray blocking member 20 is disposed at a center position of the target main body 10.

The target members 11a through 11f are required to satisfy a predetermined disposition relationship in order to effectively irradiate the primary X-rays to the target members 11a through 11f and the secondary X-rays to the sample. Hereinafter, this positional relationship of the target members will be explained with reference to FIG. 3.

Figure 3:
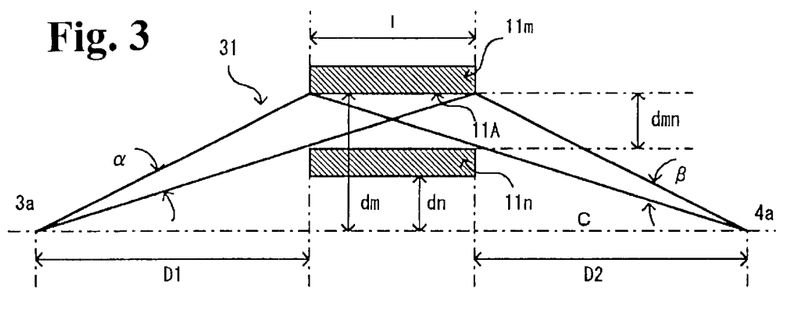
FIG. 3 is a schematic sectional view of target members of the invention.

FIG. 3 is a schematic sectional view of the target members 11, and two adjacent target members 11m and 11n are shown as an example. Each of the target members 11m and 11n has a length l in a direction of the central axis C, and a target surface 11A of the target member 11m is disposed at a position away from the central axis C for a space or length dm in the diametral direction. The target surface 11A of the target member 11n is disposed at a position away from the central axis a for a space dn in the diametral direction. The target members 11m and 11n are spaced apart from each other for a disposition interval dmn in the diametral direction. Also, the target members 11m and 11n have side ends located away from a center 3a of the X-ray source 3 for a distance D1 on the central axis C, and the opposite side ends located away from a center 4a of the sample irradiation position 4 for a distance D2 on the central axis C. The target surfaces 11A of the target members 11m and 11n are disposed parallel to the central axis C.

An angle α on a sectional surface including the central axis C in case the target surface 11A of the target member 11m is seen from the center 3a of the X-ray source 3, is determined by an angle formed between one end of the target member 11m at an X-ray source 3 side and the other end of the target member 11m at a sample irradiation position 4 side, and the angle α forms an effective solid angle a with respect to observing surfaces around the central axis C observing from the X-ray source 3. Here, in order to effectively irradiate the primary X-rays 31 to the target surface of the target member 11m, the adjacent target member 11n is required to be disposed outside the angle α (effective solid angle a), so that the target 11n does not block the primary X-rays 31. Also, it is necessary that the primary X-rays 31 do not directly reach the sample S.

Also, as in the angle α, an angle β on the sectional surface including the central axis C in case the target surface 11A of the target member 11m is seen from the center 4a of the sample irradiation position 4, is determined by an angle between the one end of the target member 11m at the X-ray source 3 side and the other end of the target member 11m at the sample irradiation position 4 side. The angle β forms an effective solid angle b with respect to observing surfaces around the central axis C observing from the sample irradiation position 4.

Here, in order to allow the secondary X-rays 32 generated in the target surface 11A to reach the sample irradiation position 4 effectively, it is necessary to dispose the adjacent target member 11n outside the angle β (effective solid angle b), so that the target member 11n does not block the secondary X-rays 32.

The length l of the target member 11 in the direction of the central axis C, and the disposition interval dmn between the target members 11m and 11n are set to satisfy the above conditions. Incidentally, the angle α (effective solid angle a), the angle β (effective solid angle b) can be determined geometrically by the length l, the disposition interval dmn, and the distances D1 and D2.

An effective solid angle A observing the target members 11 from the X-ray source 3 is formed by combining the effective solid angles a, respectively formed between the two adjacent target members, among the plural target members 11a through 11f. Here, by arranging the adjacent target members to be located outside the angle α of observing each target surface, the effective solid angle A can be a solid angle of observing a diameter of the target member 11a provided at the outermost circumference except a solid angle portion of the X-ray blocking member 20 disposed on the central axis C.

Also, an effective solid angle B of observing the target members 11 from the sample irradiation position 4 is formed by combining the effective solid angles b, which are respectively formed between the two adjacent target members, among the plural target members 11. Here, by arranging the adjacent target members to be located outside the angle β of observing each of the target surfaces, the effective solid angle B can be an angle of observing the diameter of the target member 11a provided at the outermost circumference except the solid angle portion of the X-ray blocking member 20 disposed on the central axis C.

Figure 4:
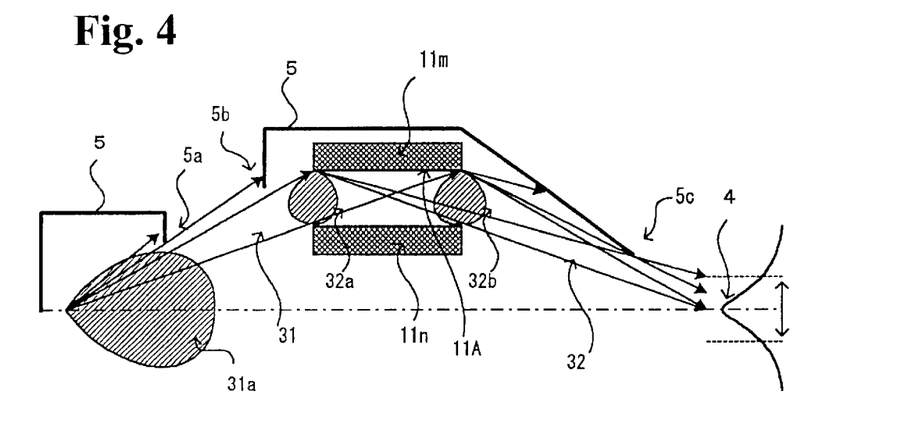
FIG. 4 is a schematic view for explaining paths in which primary X-rays and secondary X-rays pass.

Next, paths through which the primary X-rays and the secondary X-rays pass will be explained with reference to FIG. 4.

The X-ray source 3 generates the primary X-rays 31 in a certain intensity distribution (for example, an intensity distribution 31a shown in FIG. 4), and the primary X-rays 31 are emitted from the opening section 5a of the shielding member 5' toward the secondary target main body 10 side. Incidentally, the shielding member 5' of the X-ray source 3 prevents leakage of the primary X-rays toward areas other than the secondary target main body 10 side. The primary X-rays 31 radiated from the X-ray source 3 pass through the opening section 5b of the shielding member 5' surrounding a periphery of the target members 11, and are irradiated to the target surfaces 11A of the target member 11.

The primary X-rays 31, which have passed through the opening section 5b, pass through a space between the adjacent target members 11m and 11n, and are irradiated to the target surface 11A of the target member 11m. By setting the length l of the target member and the disposition interval dmn or the like to satisfy the aforementioned conditions, the target surface 11A is effectively irradiated without being blocked by the target member 11n.

In the target surface 11A, by an excitation due to the irradiated primary X-rays 31, in the certain intensity distribution (for example, intensity distributions 32a and 32b shown in FIG. 4), the secondary X-rays 32, which have a spectrum inherent to the second target material, are generated. By setting the length l and the disposition interval dmn or the like to satisfy the above conditions, among the generated secondary X-rays 32, X-rays to be transferred to the sample irradiation position 4 are directed to the sample irradiation position 4 without being blocked by the target member 11n.

Furthermore, the secondary X-rays 32 generated in the target surface 11A are narrowed down by the shielding member 5, the inner diameter of which is narrowed toward the sample irradiation position 4 direction, and are irradiated to the sample irradiation position 4 through the opening section 5c. A distribution curve shown in a right end section of FIG. 4 schematically shows an intensity distribution of the secondary X-rays which reach the sample irradiation position 4. By using the shielding member 5, the inner diameter of which is narrowed, the secondary X-rays 32 are allowed to pass through the opening section 5c with a small diameter, so that a range of an irradiation area of the secondary X-rays 32 can be narrowed, to thereby increase an analyzing sensitivity. Incidentally, broken lines and an arrow line in the distribution curve respectively show a limitation range and the irradiation area by the shielding member 5 of the target members 11. In a structure which is not provided with the shielding member 5 of the target members 11, the secondary X-rays are irradiated at the sample irradiation position 4 in a large range, so that the analyzing sensitivity is decreased.

Therefore, the shielding member 5 of the target members 11 prevents the primary X-rays from irradiating to areas other than the secondary target device 2 side, and at the same time, the shielding member 5 of the target member 11 condenses the secondary X-rays 32 toward the sample radiation position 4.

Figures 5A, 5B, 5C:
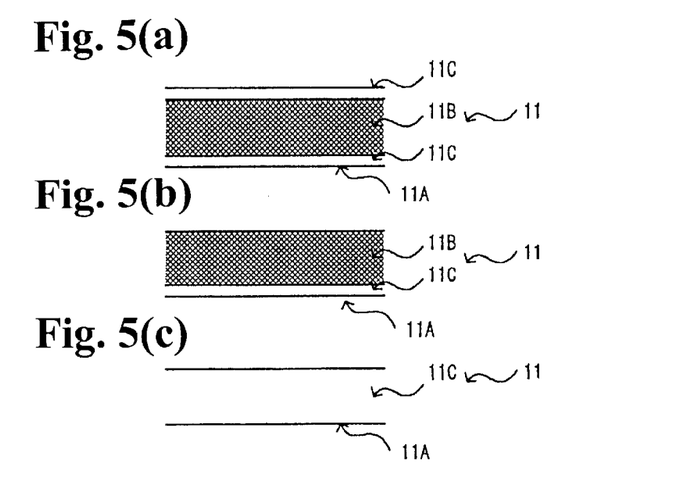
FIGS. 5(a) through 5(c) are schematic views for explaining a first example of the target member of the invention.

Next, examples of the target member will be explained with reference to FIGS. 5(a) through 5(c). FIG. 5(a) is a first example of the target member, and is formed by adhesion or vapor deposition of a secondary target material 11C on both surfaces of a substrate or base 11B made of an X-ray shielding material. The substrate 11B has a thickness which prevents the primary X-rays from passing therethrough. Also, the secondary target material 11C has preferably a film thickness which can provide enough fluorescent X-rays excited from the secondary target material by the primary X-rays, and which can provide the maximum fluorescent X-rays. Also, the thickness of the secondary target material 11C is preferable selected such that the fluorescent X-rays generated from the X-rays shielding materials of the substrate are fully absorbed therein. Further, it is desirable that the film thickness of the secondary target material 11C is considered as a bulk.

It is enough that the secondary target material 11C is provided on at least one surface of the target member 11, to which the primary X-rays are irradiated, and a surface where the primary X-rays are not irradiated can constitute a substrate surface. In a second example shown in FIG. 5(b), the secondary target material 11C is provided only on one surface of the target member 11. Also, as in a third example shown in FIG. 5(c), there can be adopted a structure formed of only the secondary target material 11C without using the substrate or base.

Figure 6A:
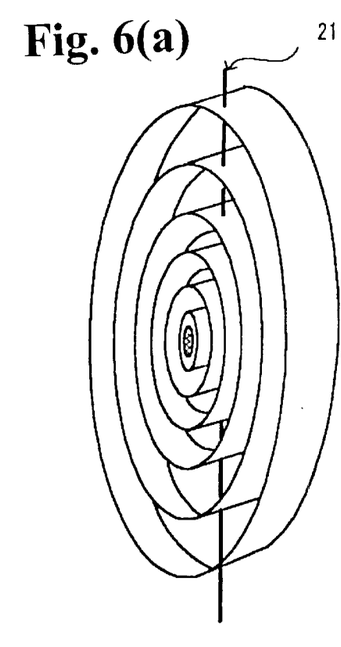
FIGS. 6(a) through 6(c) are schematic views for explaining an example of holding second target materials of the invention.
Figure 6B:
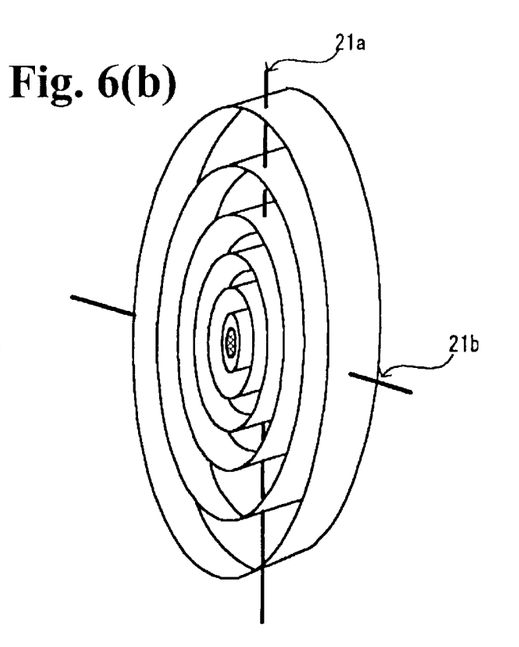

Examples of holding the secondary target members will be explained with reference to FIGS. 6(a) through 6(c). In an example of holding the secondary target materials shown in FIG. 6(a), a plurality of secondary target members 11 is held by a single supporting member 21, and the supporting member 21 formed of the X-ray shielding material is provided to pass through a center of the respective secondary target members 11. In a holding example shown in FIG. 6(b), a plurality of secondary target members 11 is held by two supporting members 21a and 21b, and the supporting members 21a and 21b formed of the X-ray shielding material pass through a center of the respective secondary target members 11 with a predetermined angle therebetween. The supporting members 21, 21a, and 21b may be formed in a shape of a wire with a small diameter, and the irradiation of the primary X-rays to the target surface is made a very small to be ignored.

Figure 6C:
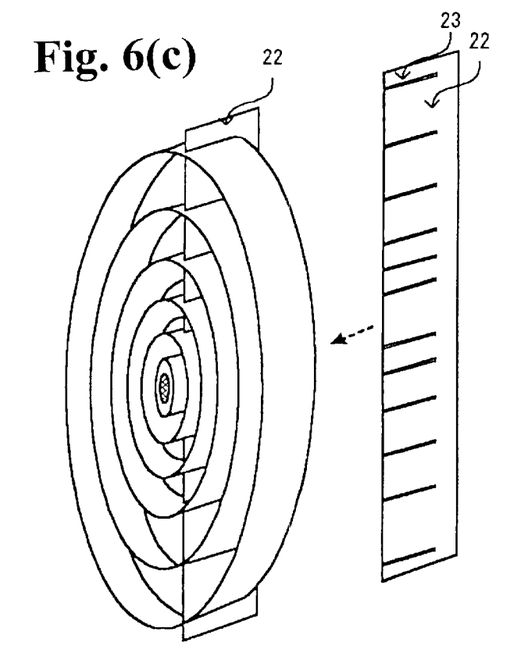

Also, in a holding example shown in FIG. 6(c), a plurality of secondary target members 11 is held by a plate-like supporting member 22, and grooves or slits 23 are formed in one side of the plate-like supporting member 22 made of the X-ray shielding material such that the grooves 23 are provided with intervals therebetween, which are the same as the disposition intervals between the secondary target members 11. By inserting the secondary target members 11 into the grooves 23 at positions such that the supporting member 22 passes through the center of the secondary target members 11, the secondary target members 11 can be held by the supporting member 22. The thickness of the supporting member 22 can be made thin sufficiently with respect to the effective solid angle, and the supporting member 22 becomes substantially parallel to a direction of irradiating the primary X-rays. Thus, prevention of the irradiation of the primary X-rays to the target surface can be made very small to be ignored. Incidentally, plural sheets of supporting members 22 may be arranged to cross each other at the center position of the secondary target members 11 by using the plural sheets of the supporting members 22.

Figure 7:
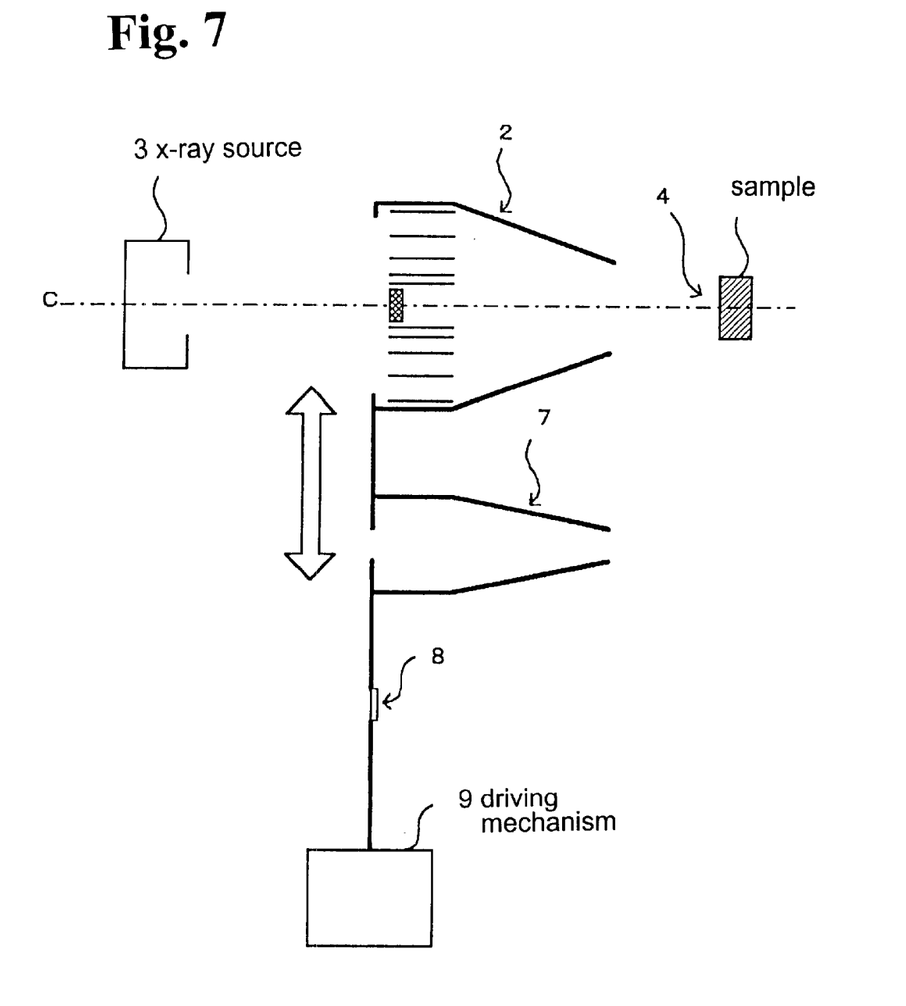
FIG. 7 is a schematic view for explaining a mechanism of switching irradiated X-rays.

Next, the fluorescent X-ray analyzing apparatus of the invention has a structure such that the secondary X-rays and the primary X-rays are switched for irradiation to the sample. FIG. 7 is a schematic view for explaining a mechanism of switching the irradiated X-rays. In FIG. 7, in addition to the secondary target device 2 of the invention, there are disposed a collimator 7 which irradiates the primary X-rays to the sample directly, and a filter 8 for absorbing a part of the primary X-rays. The collimator 7 and the filter 8 can be switched by a driving mechanism 9. Incidentally, one or both of the collimator 7 and the filter 8 may be provided.

The driving mechanism 9 moves the secondary target device 2, the collimator 7, and the filter 8 on the central axis C connecting between the X-ray source 3 and the sample irradiation position 4. In case a direct excitation by the primary X-rays is carried out by directly irradiating the primary X-rays to the sample S, the collimator 7 is disposed on the central axis C. Also, in case X-rays with specific wavelength are irradiated to the sample S by absorbing a part of the primary X-rays, or in case of using a primary X-ray filtering method where a background of an object element is decreased, the filter 8 is disposed on the central axis C.

Also, in case the secondary target device 2 is disposed, by generating fluorescent X-rays including characteristic X-rays inherent to the secondary target, continuous X-rays contained in the primary X-rays are decreased, and the signal-to-noise (S/N) ratio of the fluorescent X-rays from the sample is improved, to thereby achieve a highly sensitive detection of the micro-elements.

Next, other examples of the target member applied to the secondary target device of the invention will be explained with reference to FIG. 8 through FIG. 10(b). Incidentally, the target member shown in FIG. 2 constitutes a first example.

Figure 8:
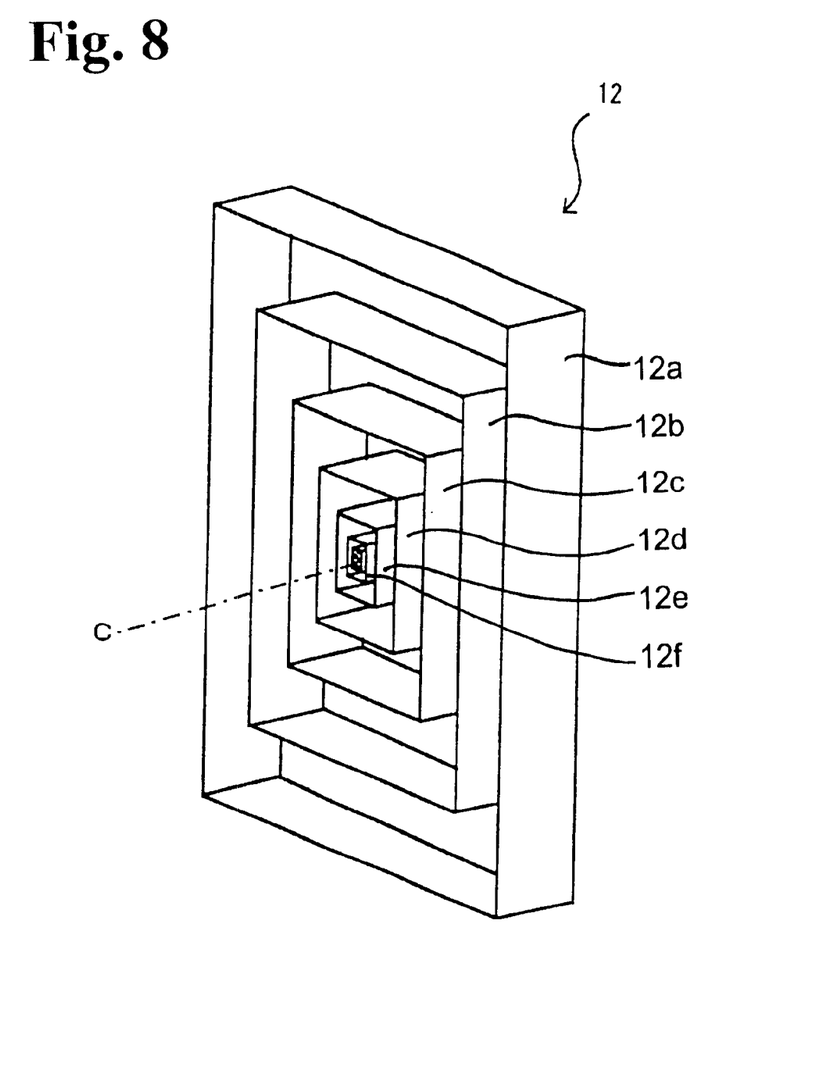
FIG. 8 is a schematic view for explaining another example of a target main body applied to the secondary target device of the invention.

As shown in FIG. 8, in a second example of a target member, a shape of a secondary target member 12 is a polygon.

Secondary target members 12a through 12f are formed in polygonal shapes having different side lengths, and disposed such that respective center positions of the target members coincide with the central axis C.

In the third to seventh examples of the target member, divided secondary target members are assembled. In the third example shown in FIG. 9(a), secondary target members 13 formed into sector shapes by dividing a circumference at predetermined angels are assembled, and in the fourth and fifth examples respectively shown in FIG. 9(b) and FIG. 9(c), secondary target members 14 and 15 formed into rectangular shapes are assembled radially from the central axis, respectively.

Figure 9A:
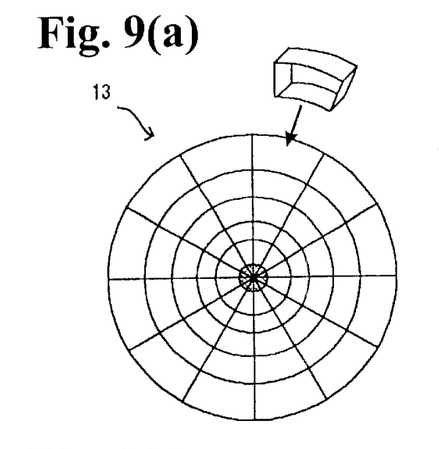
FIGS. 9(a) through 9(e) are schematic views for explaining a still another example of the target main body applied to the secondary target device of the invention.
Figure 9B:
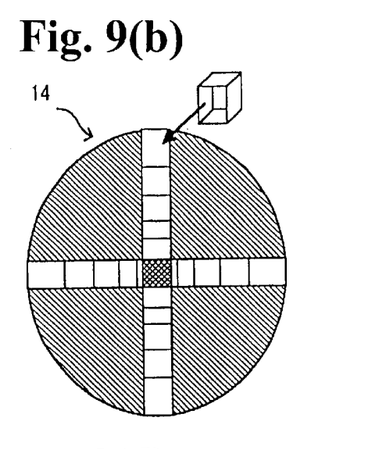
Figure 9C:
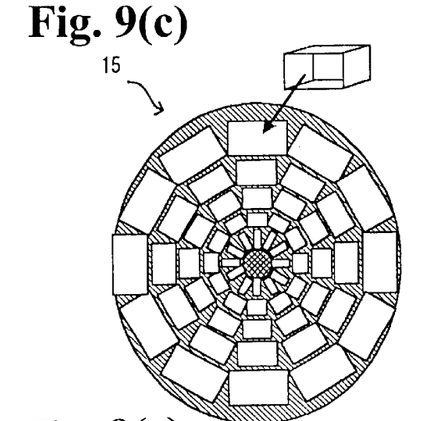
Figure 9D:
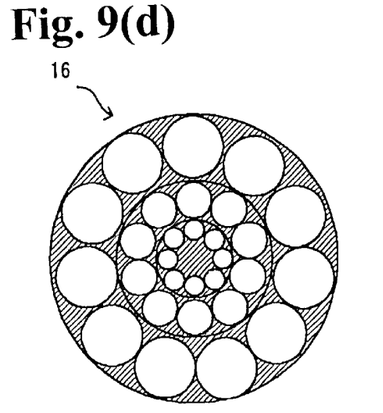
Figure 9E:
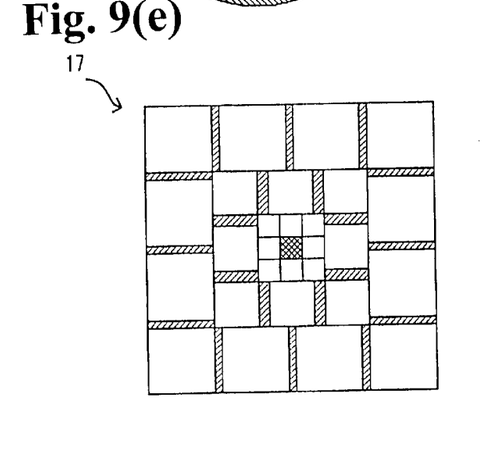

Also, FIGS. 9(d) and 9(e) show conditions of secondary target members 16 and 17, respectively, seen from the X-ray source side in the sixth and seventh examples. In the sixth example, the secondary target members 16 having sections in circular shapes are arranged around the central axis, and in the seventh example, the secondary target members 17 having sections in rectangular shapes are arranged around the central axis.

Figure 10A:
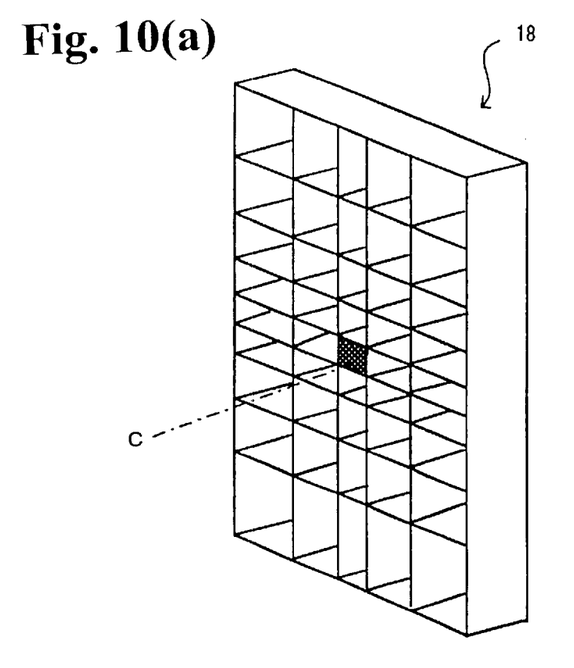
FIGS. 10(a) and 10(b) are schematic views for explaining a still further example of the target main body applied to the secondary target device of the invention.
Figure 10B:
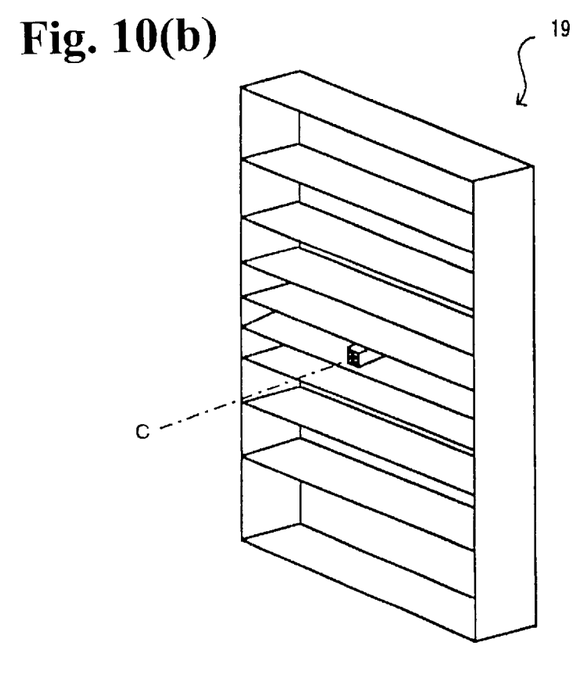

In the eighth and ninth examples of the target member, secondary target members 18 and 19 shown in FIGS. 10(a) and 10(b) are respectively divided in lateral and vertical directions, and divided in a lateral direction (or vertical direction).

As in the first example, in the respective divided target members shown in the third through seventh examples and the respective divided target members shown in the eighth and ninth examples, the length in the central axis direction and disposition intervals in the diametral direction between the adjacent target members are formed to satisfy the first condition, in which an effective solid angle of observing the target surface from the primary X-ray source coincides with an effective solid angle of observing a space between the target member and an adjacent target member at the side of the target surface from the primary X-ray source side, and a second condition, in which an effective solid angle of observing the target surface from the sample irradiation position coincides with an effective solid angle of observing the space between the target member and the adjacent target member from the sample irradiation position.

As described above, according to the target device of the invention, the X-ray irradiating condition can be maintained constant in case of switching the irradiated X-rays, and at the same time, enough secondary X-rays can be irradiated to the sample. Also, the secondary X-rays can be irradiated to a minute portion of the sample.

Also, according to the fluorescent X-ray analyzing apparatus of the invention, the X-ray irradiating condition can be maintained constant in case of switching the irradiated X-rays, and at the same time, enough secondary X-rays to be irradiated to the sample can be obtained to thereby improve the detection sensitivity. Further, an analyzing sensitivity with respect to the minute portion of the sample can be increased.

While the invention has been explained with reference to the specific embodiments of the invention, the explanation is illustrative and the invention is limited only by the appended claims.

What is claimed is:

1. A secondary target device for transferring primary X-rays generated at a primary X-ray source to a sample as secondary X-rays, comprising:

a target main body including a plurality of target members having target surfaces facing a central axis linking between the primary X-ray source and the sample, and secondary target materials formed on the target surfaces, said plurality of target members being disposed concentrically with respect to the central axis to be spaced apart from each other, each of the target members having a length in a direction along the central axis and a disposition interval relative to a target member adjacent thereto to satisfy a first condition for allowing the primary X-rays to enter the target surface and a second condition for allowing the secondary X-rays generated at the target members by incidence of the primary X-rays to enter the sample, and an X-ray blocking member disposed on the central axis for blocking an irradiation of the primary X-rays from the primary X-ray source to the sample.

2. A secondary target device according to claim 1, wherein in said first condition, an effective solid angle of observing one target surface of one target member from the primary X-ray source coincides with an effective solid angle of observing a space between said one target member and an adjacent target member located inside said one target member from the primary X-ray source, and in the second condition, an effective solid angle of observing the target surface of said one target member from the sample coincides with an effective solid angle of observing the space between said one target member and said adjacent target member from the sample.

3. A secondary target device according to claim 2, wherein said target members are arranged have front and back edges facing the X-ray source and the sample, respectively, said front and back edges of the target members being disposed parallel to each other.

4. A secondary target device according to claim 3, wherein said target members are spaced apart from each other with different distances.

5. A secondary target device according to claim 4, further comprising at least one support member for connecting the target members to be spaced apart from each other.

6. A secondary target device according to claim 5, wherein said target surfaces are arranged parallel to the central axis.

7. A fluorescent X-ray analyzing apparatus, comprising:

a primary X-ray source for generating primary X-rays, a secondary target device for receiving the primary X-rays and providing fluorescent X-rays to a sample, said secondary target device including a target main body located near the primary X-ray source, and an X-ray blocking member disposed on a central axis linking between the primary X-ray source and the sample to prevent the primary X-rays from the primary X-ray source from being irradiated to the sample, said target main body including a plurality of target members having target surfaces facing the central axis and secondary target materials formed on the target surfaces, said plurality of target members being disposed concentrically with respect to the central axis to be spaced apart from each other, each of the target members having a length in a direction along the central axis and a disposition interval relative to a target member adjacent thereto to satisfy a first condition for allowing the primary X-rays to enter the target surface and a second condition for allowing the secondary X-rays generated at the target members by incidence of the primary X-rays to enter the sample, and an X-ray detector for detecting fluorescent X-rays generated from the sample.

8. A fluorescent X-ray analyzing apparatus according to claim 7, wherein in said first condition, an effective solid angle of observing one target surface of one target member from the primary X-ray source coincides with an effective solid angle of observing a space between said one target member and an adjacent target member located inside said one target member from the primary X-ray source, and in the second condition, an effective solid angle of observing the target surface of said one target member from the sample coincides with an effective solid angle of observing the space between said one target member and said adjacent target member from the sample.

9. A fluorescent X-ray analyzing apparatus according to claim 8, further comprising a first shielding member surrounding said periphery of the target members, said first shielding member having opening sections on the central axis, one of the opening sections limiting an area of irradiating the secondary X-rays in the sample.

10. A fluorescent X-ray analyzing apparatus according to claim 9, further comprising a second shielding member surrounding the X-ray source for irradiating the primary X-rays to the target members.

11. A fluorescent X-ray analyzing apparatus according to claim 8, further comprising at least one of a collimator for directly irradiating the primary X-rays to the sample and a filter for absorbing a part of the primary X-rays, one of said secondary target device, the collimator and the filter being disposed on the central axis.

12. A fluorescent X-ray analyzing apparatus according to claim 11, further comprising a driving device for disposing one of the secondary target device, the collimator, and the filter on the central axis.

* * * * *